(12) United States Patent  
Margrain (10) Patent No.: US 11,903,648 B2  
(45) Date of Patent: Feb. 20, 2024

(54) METHOD AND APPARATUS FOR DETERMINING A SCATTERING SPECTRUM OF AN EYE

(71) Applicant: UNITED KINGDOM RESEARCH AND INNOVATION, Swindon (GB)

(72) Inventor: Tom Margrain, Cardiff (GB)

(73) Assignee: UNITED KINGDOM RESEARCH AND INNOVATION (GB)

( * ) Notice: Subject to any disclaimer, the term of this patent is extended or adjusted under 35 U.S.C. 154(b) by 497 days.

(21) Appl. No.: 17/278,256

(22) PCT Filed: Sep. 19, 2019

(86) PCT No.: PCT/GB2019/052637  
§ 371 (c)(1),  
(2) Date: Mar. 19, 2021

(87) PCT Pub. No.: WO2020/058717  
PCT Pub. Date: Mar. 26, 2020

(65) Prior Publication Data  
US 2021/0353140 A1 Nov. 18, 2021

(30) Foreign Application Priority Data

Sep. 21, 2018 (GB) ...................................... 1815374

(51) Int. Cl.  
*A61B 3/12* (2006.01)  
*G16H 50/50* (2018.01)  
(Continued)

(52) U.S. Cl.  
CPC .............. *A61B 3/12* (2013.01); *A61B 3/0025* (2013.01); *A61B 3/14* (2013.01); *G06T 7/0014* (2013.01);  
(Continued)

(58) Field of Classification Search  
CPC .......... A61B 3/12; A61B 3/0025; A61B 3/14; A61B 3/10; A61B 3/0008; G06T 7/0014;  
(Continued)

(56) References Cited

U.S. PATENT DOCUMENTS

2012/0092619 A1 4/2012 Rowe  
2013/0301004 A1 11/2013 Kahn et al.  
(Continued)

FOREIGN PATENT DOCUMENTS

DE 10 2007 025 425 A1 12/2008  
DE 10 2007 047 300 A1 4/2009  
(Continued)

*Primary Examiner* — Mohammed A Hasan  
(74) *Attorney, Agent, or Firm* — Cowan, Liebowitz & Latman, P.C.; Mark Montague (57) ABSTRACT

Embodiments of the present invention provide a computer-implemented method of determining a scattering spectrum of an eye. The method comprises receiving data from a detector indicative of a reflected wave of radiation reflected from the retina, wherein the reflected wave of radiation is formed by an incident wave of masked radiation directed towards a retina of the eye, such that at least one region masked from the incident wave is present on the retina, determining a first back scattering spectrum indicative of light scattered from an optical media of the eye in dependence on a portion of the reflected wave of radiation corresponding to the at least one masked region, determining a second back scattering spectrum indicative of light scattered from a neural retina of the eye in dependence on retinal structure information representative of neural retinal structure, and determining the scattering spectrum of the eye in dependence on the first back scattering spectrum and the second back scattering spectrum.

22 Claims, 9 Drawing Sheets

(51) Int. Cl.
  *A61B 3/00* (2006.01)
  *A61B 3/14* (2006.01)
  *G06T 7/00* (2017.01)
  *G06T 11/00* (2006.01)
(52) U.S. Cl.
  CPC ........... *G06T 11/005* (2013.01); *G16H 50/50* (2018.01); *G06T 2207/10101* (2013.01); *G06T 2207/20084* (2013.01); *G06T 2207/30041* (2013.01)
(58) Field of Classification Search
  CPC ......... G06T 11/005; G06T 2207/10101; G06T 2207/20084; G06T 2207/30041; G16H 50/50
  USPC .......................................................... 351/206
  See application file for complete search history.

(56) References Cited

U.S. PATENT DOCUMENTS

| | | |
|---|---|---|
| 2013/0321764 A1 | 12/2013 | O'Brien et al. |
| 2016/0120400 A1* | 5/2016 | Mohr ....................... A61B 3/14 351/246 |
| 2018/0228367 A1 | 8/2018 | Hathaway et al. |
| 2022/0328177 A1* | 10/2022 | Ivanovska .............. G16H 40/60 |
| 2022/0370138 A1* | 11/2022 | Shelton, IV ........... A61B 34/30 |
| 2023/0053497 A1* | 2/2023 | Sarwar .................... G06T 7/246 |

FOREIGN PATENT DOCUMENTS

| | | | |
|---|---|---|---|
| DE | 10 2007 053 386 A1 | 5/2009 | |
| DE | 102007053386 A1 * | 5/2009 | ........... A61B 3/1173 |
| WO | 2009/046912 A1 | 4/2009 | |

* cited by examiner

410 – Checker Mask

420 – Bar Mask

METHOD AND APPARATUS FOR DETERMINING A SCATTERING SPECTRUM OF AN EYE

BACKGROUND

Age-related macular degeneration (AMD) is the developed world's leading cause of sight loss. Diagnosis and monitoring of conditions such as AMD is improved by the measurement of the optical density (OD) of visual pigments within the retina, i.e. the degree to which the retina retards transmitted rays of light. It is therefore important for these OD measurements to be as accurate as possible.

The OD of visual pigments may be calculated by measuring a reflectance of the retina in both a dark adapted (after a period of adaptation to darkness) and a 'bleached' (after exposure to bright light) state. The OD may then be calculated from a difference between the two states.

Acquisition of accurate retinal reflectance data is therefore requisite. However, light directed at the eye will be reflected from several different layers of the eye, including the sclera, retinal pigment epithelium, neural retina and ocular media. This makes accurate measurement of retinal reflectance difficult. Noise and spectral shifts caused by pre-retinal scattering of light within the eye hamper the acquisition of quality retinal reflectance data.

It is an object of embodiments of the invention to improve the accuracy of OD measurements.

SUMMARY OF THE INVENTION

According to aspects of the present invention there is provided methods, apparatus and computer software as defined in the claims appended thereto.

According to aspects of the present invention there is provided a computer-implemented method of determining a scattering spectrum of an eye, comprising determining a first back scattering spectrum indicative of light scattered from an optical media of the eye in dependence on a portion of a reflected wave of radiation, determining a second back scattering spectrum indicative of light scattered from a neural retina of the eye in dependence on retinal structure information representative of neural retinal structure, and determining the scattering spectrum of the eye in dependence on the first back scattering spectrum and the second back scattering spectrum.

BRIEF DESCRIPTION OF THE DRAWINGS

Embodiments of the invention will now be described by way of example only, with reference to the accompanying figures, in which.

DETAILED DESCRIPTION OF EMBODIMENTS OF THE INVENTION

Figure 1:
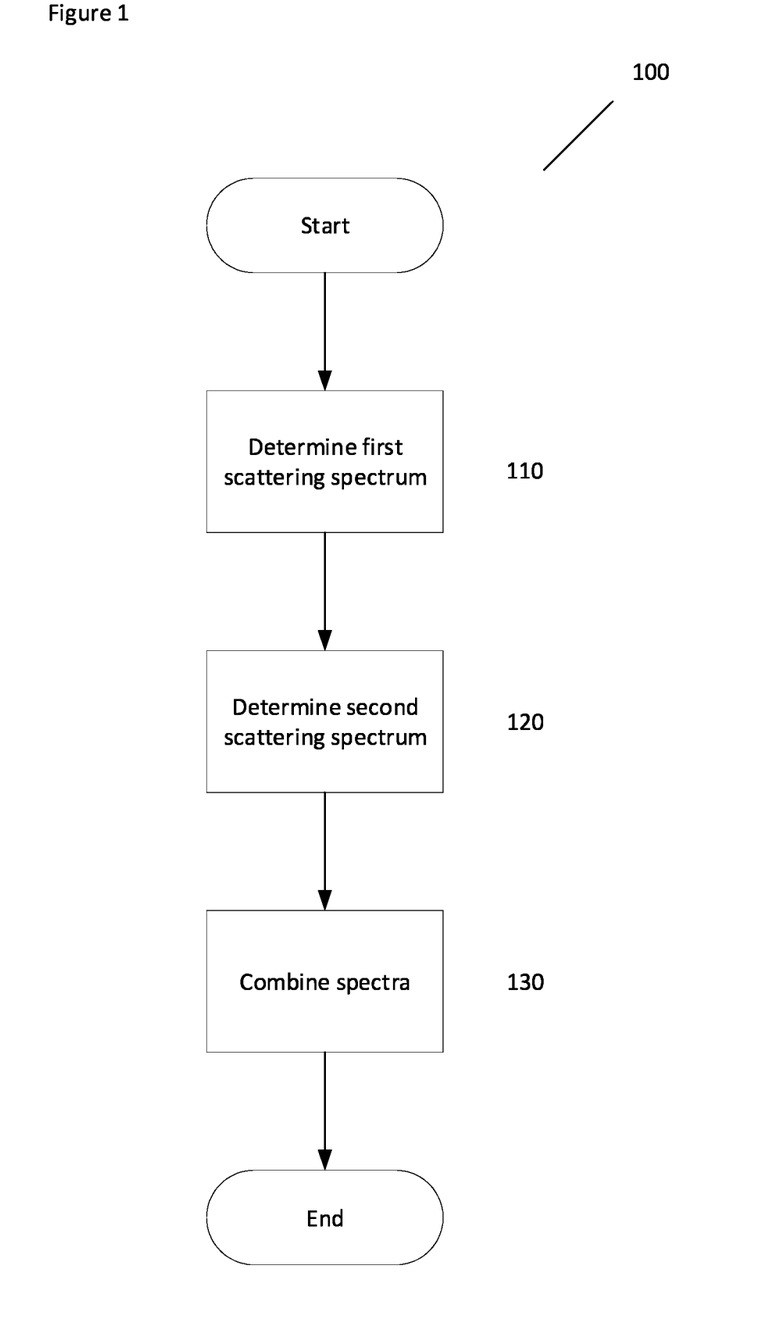
FIG. 1 shows a method according to an embodiment of the invention.

FIG. 1 illustrates a method 100 according to an embodiment of the invention. The method 100 is a method for determining a scattering spectrum of an eye of a subject. The resultant scattering spectrum may be used to, for example, correct reflectance data from the eye to obtain a reflectance spectrum that more accurately represents reflectance from tissue posterior to a photoreceptor inner, outer-segment junction of the eye.

The method 100 comprises a step 110 of determining a first back scattering spectrum, as will be explained. The first back scattering spectrum may be indicative of light scattered from one or more ocular media, i.e. one or more transparent components of the eye. For example, the first back scattering spectrum may be indicative of light scattered from a lens of the eye.

The method 100 comprises a step 120 of determining a second back scattering spectrum, as will be explained. The second back scattering spectrum may be indicative of light scattered from a neural retina of the eye. Step 120 may be carried out before step 110, after step 110, or concurrently to step 110.

The method 100 comprises a step 130 of combining the first back scattering spectrum and the second back scattering spectrum to produce a scattering spectrum of the eye. The spectra may be combined linearly, for example $$R_{scat}(\lambda)=RM_{scat}(\lambda)+RN_{scat}(\lambda)$$

Where $R_{scat}(\lambda)$ is the scattering spectrum of the eye, $RM_{scat}(\lambda)$ is the first back scattering spectrum and $RN_{scat}(\lambda)$ is the second back scattering spectrum. However other combinations can also be envisaged, for example one or both of the first and second back scattering spectra may be associated with a respective weighting.

Figure 2:
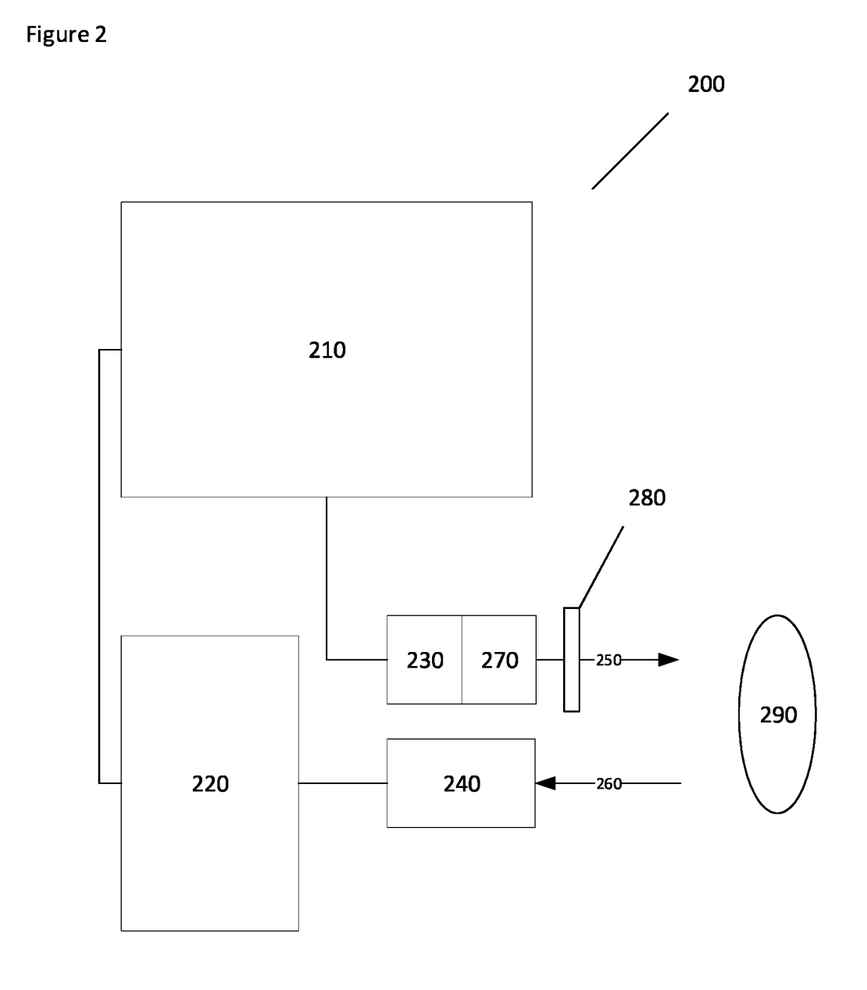
FIG. 2 shows a schematic diagram of an embodiment of the invention.

Elements of the method 100 may be carried out at one or more components of an apparatus 200, schematically illustrated in FIG. 2 according to an embodiment of the invention.

The apparatus 200 comprises a radiation source 230. The radiation source 230 may be arranged to emit an incident radiation 250, which may be EM radiation in the visible range, however other radiation types can also be envisaged. For example, in some embodiments the radiation source 230 may be a bulb, or a light emitting array. The radiation source 230 may be configured to direct the incident radiation 250 towards a target 290, for example a retina of an eye. For example, if the radiation source 230 is a light emitting array, the array may be configured to selectively emit the incident radiation 250 in the direction of the target 290. The apparatus 200 may optionally further comprise a directing apparatus 270 for the radiation source 230. The directing apparatus 270 may be configured to direct the incident radiation 250 towards a target. For example, the directing apparatus may be a lens or other refracting or reflective device.

The apparatus 200 may comprise a mask 280 for the incident radiation 250, such that the field of the incident radiation 250 comprises at least one masked segment, which generally blocks radiation, and at least one unmasked segment, wherein the unmasked segment generally allows radiation to pass through the mask. The mask 280 may be integrated within the radiation source 230 or the directing apparatus 270 or may be applied to the incident radiation 250 subsequently to emission by the radiation source. For example, in an embodiment of the invention the radiation source 230 may be an N×M array of light emitting devices. The mask 280 may be a configuration applicable to the array of light emitting devices such that a number fewer than the total of the light emitting devices are selectively illuminated. In another embodiment of the invention the radiation source 250 may be a uniform light source, such as a bulb. The mask 280 may then be a physical barrier selectively allowing through a portion of incident radiation 250, while selectively blocking a further portion of incident radiation 250.

Application of the mask 280 therefore allows the incident radiation 250 to fall on at least a first segment of the target 290 (an 'unmasked' segment) while blocking the incident radiation 250 from falling on at least a second segment of the target 290 (a 'masked' segment).

The apparatus 200 may comprise a control unit 210 for controlling aspects of the radiation source 230. The control unit 210 may comprise software and hardware, for example a number of processors, memories and interfaces. The control unit 210 may control the time at which the radiation source 230 produces radiation, the direction of the radiation 250, and other features of the radiation 250 such as its frequency and amplitude. The control unit 210 may be operable to selectively apply the mask 280. The control unit 210 may be operable to configure the mask 280, for example to configure the number and location of the masked and unmasked segments. The control unit 210 may be controlled in part by a user, for example via a user interface. The control unit 210 may also be controlled in part by executable software either running on or communicable with the hardware of control unit 210.

The apparatus 200 may comprise a detector 240. The detector 240 may be configured to detect an intensity of a reflected radiation 260. The reflected radiation 260 may have been reflected from the target of incident radiation 250. For example, if the target of radiation 250 is an eye, incident radiation 250 will be directed towards the eye, and subsequently incident radiation 250 will be partially reflected by elements of the eye to form reflected radiation 260. The detector 240 may be a CCD (charge coupled device) or other segmented detector operable to detect an intensity of received radiation at one or more spatial location. The detector 240 may be operable to output a signal indicative of the intensity of the reflected radiation 260 at each spatial location.

The detector 240 may be communicable with an analysis unit 220 comprising a memory, and a processor operable to execute computer readable instructions which may be stored in the memory. The detector 240 may be configured to send the signal indicative of the intensity of the reflected radiation 260 at each spatial location to the analysis unit 220, which may be operable to store the signal in memory. The analysis unit 220 and the control unit 210 may be integrated components, or they may be separate. For example, the analysis unit 220 and the control unit 210 may both operate on one computer. Alternately, the analysis unit 220 and the control unit 210 may be separate and communicable. The analysis unit 220 may perform several steps of methods 110, 120 and 130.

As mentioned, the method 100 comprises a step 110 of determining a first back scattering spectrum. The first back scattering spectrum may be indicative of light scattered from one or more ocular media, i.e. one or more transparent components of the eye. For example, the first back scattering spectrum may be indicative of light scattered from a lens of the eye. Step 110 may comprise several sub-steps, as outlined in FIG. 3.

Figure 3:
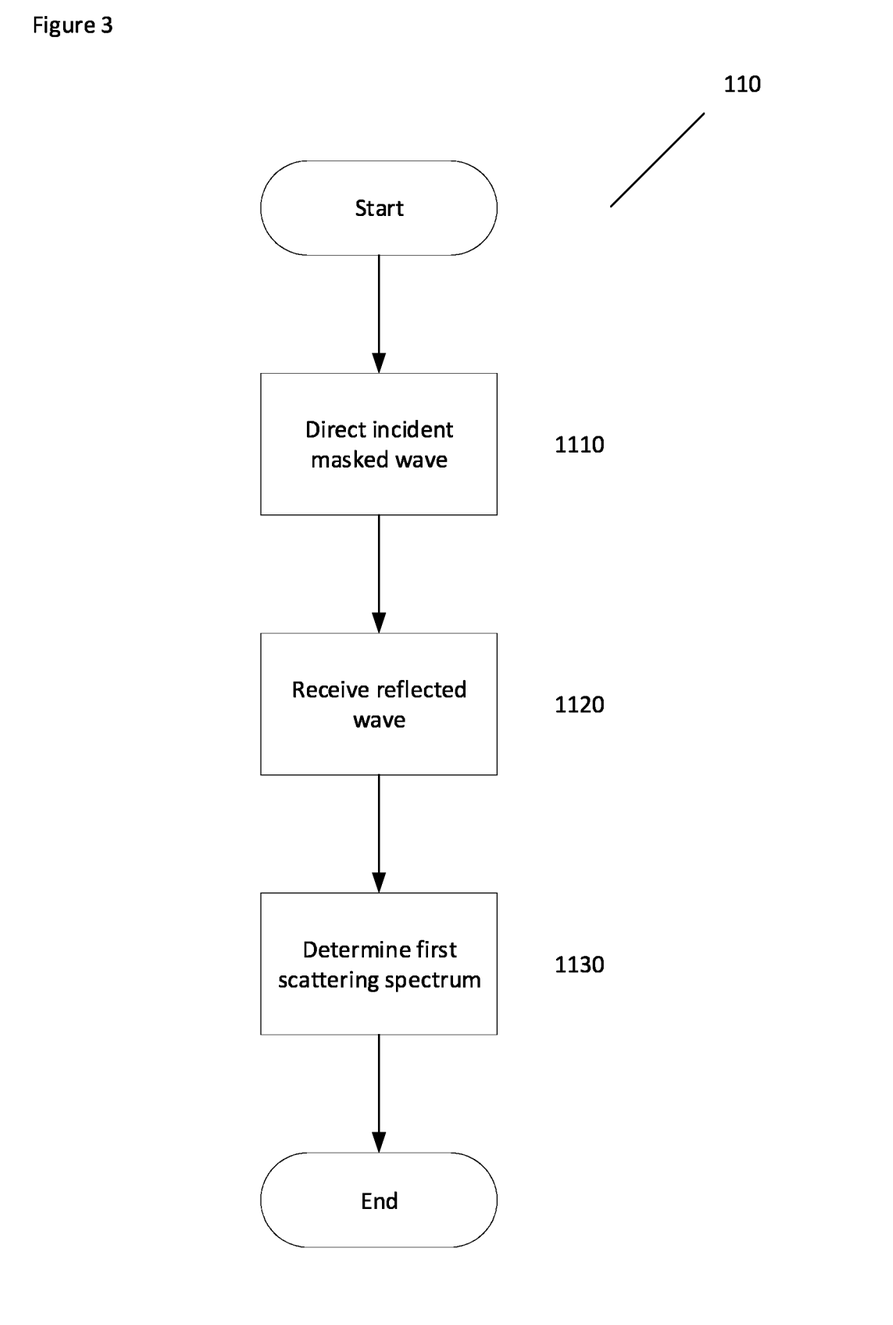
FIG. 3 shows a method according to an embodiment of the invention.

Step 110 may comprise a sub-step 1110 of directing an incident masked wave. Sub-step 1110 may be implemented by the control unit 210 and the radiation source 230. Control unit 210 may control one or more of the radiation source 230 and the directing apparatus 270 to direct an incident wave of radiation 250 towards the target 290, for example towards a retina of an eye.

A configuration of the mask 280 may be selected or applied by the control unit 210, such that the field of the incident radiation 250 comprises at least one masked segment. Application of the mask 280 allows the incident radiation 250 to fall on at least a first segment of the target 290 (an 'unmasked' segment) while blocking the incident radiation 250 from falling on at least a second segment of the target 290 (a 'masked' segment). For example, in one embodiment the mask 280 may be a configuration of the radiation source 230 or directing apparatus 270 such that the incident radiation 250 is directed to the at least one unmasked segment of the target and not towards the at least one masked segment. In another embodiment, a physical mask may be arranged between the radiation source 230 and the target which selectively blocks the incident wave from falling on the at least one masked segment of the target. For instance, if the incident wave of radiation 250 is visible light, then the at least one masked segment will not be illuminated by the incident light 250. When reference is made to 'illumination' or 'light' it will be understood that these terms could be replaced with other forms of EM or non-EM radiation in alternate embodiments.

Figure 4:
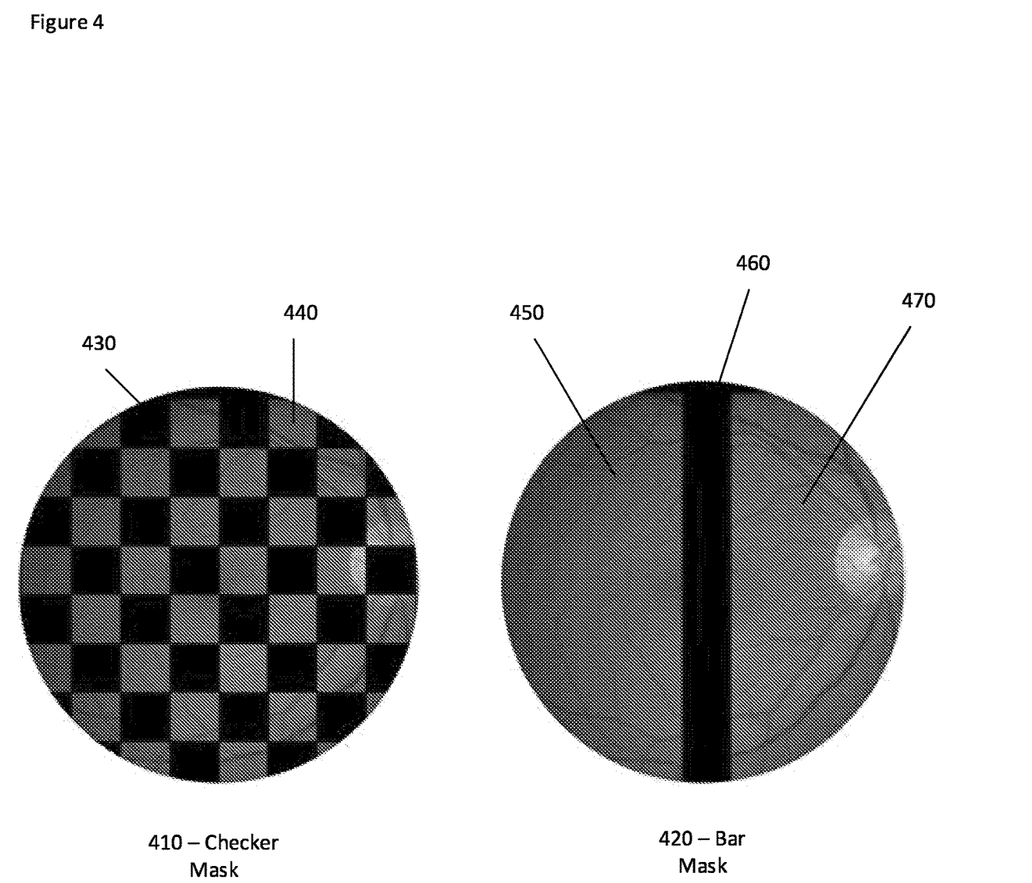
FIG. 4 shows an illustration of two illumination masks according to different embodiments of the invention.

Many different mask patterns can be envisaged. Two different mask embodiments 410, 420 according to the present invention are illustrated in FIG. 4. A first embodiment 410 and a second embodiment 420 each illustrate an image of a retina overlaid with a mask. The masked regions are represented in FIG. 4 as dark regions, examples of which are labelled 430, 460. Examples of unmasked regions are labelled 440, 450, 470. The first embodiment 410, also referred to as a checker mask, is arranged such that a plurality of masked regions (e.g. 430) alternate spatially across the target with unmasked regions (e.g. 440) in a checker pattern. The second embodiment 420, also referred to as a bar mask is arranged such that at least one masked region 460 extends across the target in a bar pattern between two unmasked regions 450, 470. It will be appreciated that the number and arrangement of masked regions may vary.

Step 110 may comprise a sub-step 1120 of receiving a reflected wave. The incident radiation 250 is reflected and scattered by different components of the eye, and the reflected radiation 260 enters the detector. As mentioned, the detector 240 may be a CCD (charge coupled device) or other segmented detector operable to detect an intensity of the received radiation at one or more spatial location. Sub-step 1120 may then comprise outputting a reflectance signal indicative of the intensity of the reflected radiation 260 at each spatial location. Sub-step 1120 may comprise mapping the reflectance signal at each spatial location to a location on the spatial pattern of mask 280, for example the checker pattern or the bar pattern shown in first and second embodiments 410 and 420. The spatial pattern, as mentioned, is indicative of which segments of the retina are masked from the incident wave.

Advantageously, the reflectance signal corresponding to each point in a masked segment on the mask may be used to determine the first scattering spectrum, as the signal at these points will not contain light directly reflected from the masked portions of the retina, as these portions of the retina were masked from the incident radiation.

Step 110 may comprise a sub-step 1130 of determining a first back scattering spectrum. The first back scattering spectrum may be indicative of light scattered from the ocular media of the eye, for example the lens of the eye. Sub-step 1130 may comprise selecting a reflectance signal corresponding to at least one point in a masked region as received in step 1120. For example, the reflectance signal may correspond to the centre of bar mask 420, though any location within a masked region may be used. In this case, the reflectance signal corresponding to the centre of bar mask 420 will be indicative of scattered light, as this portion of the retina was masked from illumination.

Sub-step 1130 may comprise selecting just one point of the mask, or a plurality of points of the mask. If more than one point is selected, sub-step 1130 may comprise calculating an average or other combination of the reflectance signal over the plurality of points of the mask. In this way, the first back scattering spectrum will be assumed to be spatially uniform over the plurality of points.

Sub-step 1130 may comprise selecting a plurality of areas of the mask to produce a spatially non-uniform back-scattering spectrum. For example, each masked checker segment in checker mask 410 may be separately selected, and a back-scattering spectrum may be uniquely determined for each checker segment. For each segment, the reflectance signal from one point may be selected to determine the back-scattering spectrum for the segment. Alternately, a plurality of points within the area may be selected and a back-scattering spectrum for the area may be derived as an average or other combination of the reflectance signal from each of the plurality of points.

Sub-steps 1110 to 1130 may be repeated at a plurality of wavelengths of light. In this way, a back-scattering spectrum as a function of wavelength may be determined. Each wavelength selected in sub-step 1110 may be below a chosen threshold wavelength. The threshold wavelength may be indicative of a threshold below which the reflectance signal from masked segments is dominated by scattered light from the optical media.

Above this threshold, the reflectance signal may be dominated by, for example, light originating within deeper layers of the retina. This threshold may be selected to be around 590 mm, as the retina reflects relatively little light at wavelengths less than this threshold. At wavelengths above this threshold the signal may primarily originate from light originating from the deeper layers of the retina, due to the optical density of blood and melanin reducing significantly with increased wavelength.

Sub-step 1130 may comprise a step of extrapolating the first back-scattering spectrum to one or more higher wavelengths. This may be done, for example, with a Mie scattering model.

Figure 5:
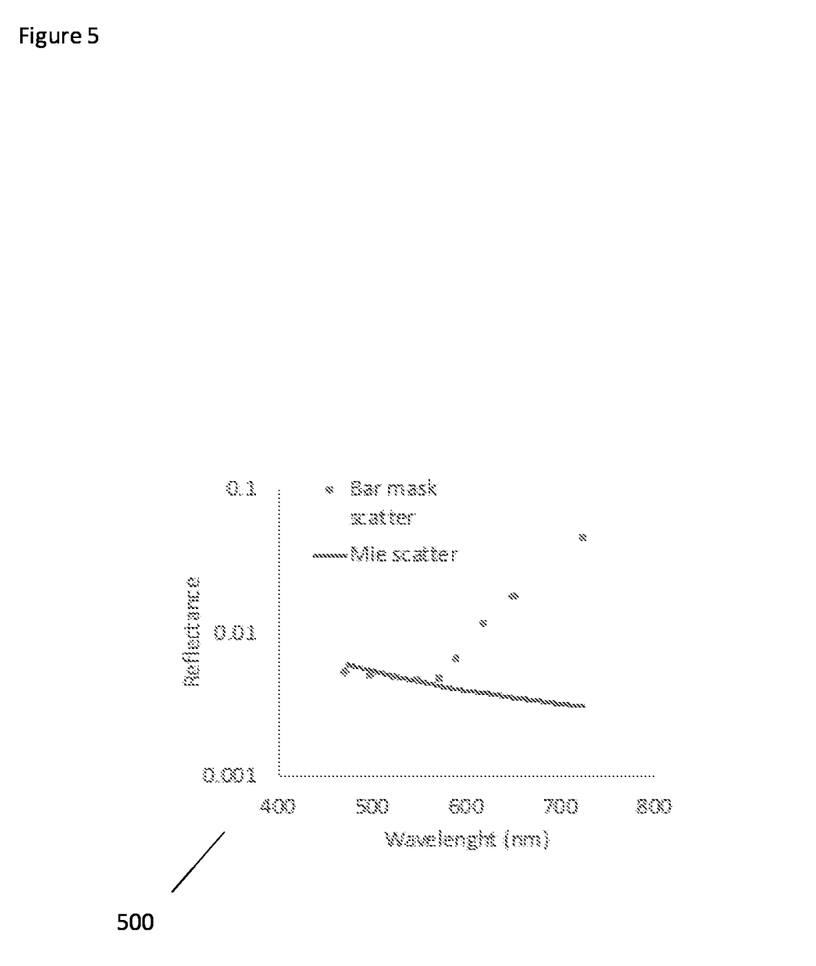
FIG. 5 shows a first scattering spectrum and a Mie scattering model according to an embodiment of the invention.

FIG. 5 shows a first back-scattering spectrum 500 produced by an embodiment of the present invention. The data points indicate measured reflectance at a masked point of the bar mask 420. As is illustrated, at wavelengths under 590 nm the measured reflectance is dominated by scattering from the optical media. Above this threshold, the reflectance spectrum becomes dominated by light originating deeper within the retina. To obtain an accurate back-scattering spectrum indicative of scattering within the optical media, the reflectance measurements taken below the threshold may be extrapolated to higher wavelengths. This extrapolation assumes that the scattering profile from the optical media follows a pre-defined scattering profile with increased wavelength, which for example may be a Mie scattering spectrum, as illustrated by the solid line on spectrum 500.

As mentioned, the method 100 comprises a step 120 of determining a second back scattering spectrum. The second back scattering spectrum may be indicative of light scattered from a neural retina of the eye. In some embodiments the second back-scattering spectrum may be previously derived and stored in a memory accessible to control unit 210. Step 120 may then comprise retrieving the second back-scattering spectrum. In other embodiments step 120 may comprise one or more sub-steps, as are outlined in FIG. 6.

Figure 6:
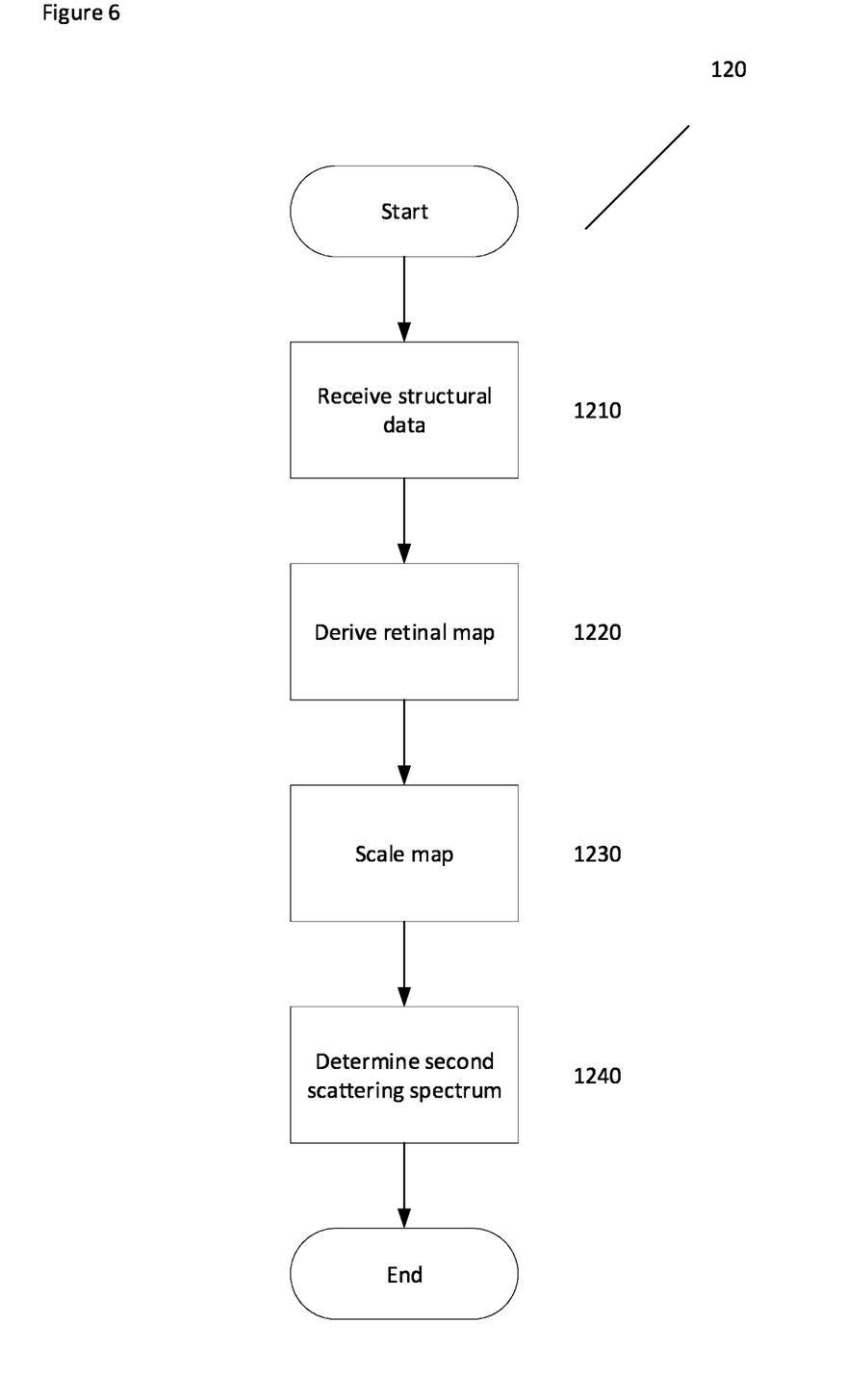
FIG. 6 shows a method according to an embodiment of the invention.
Figure 7:
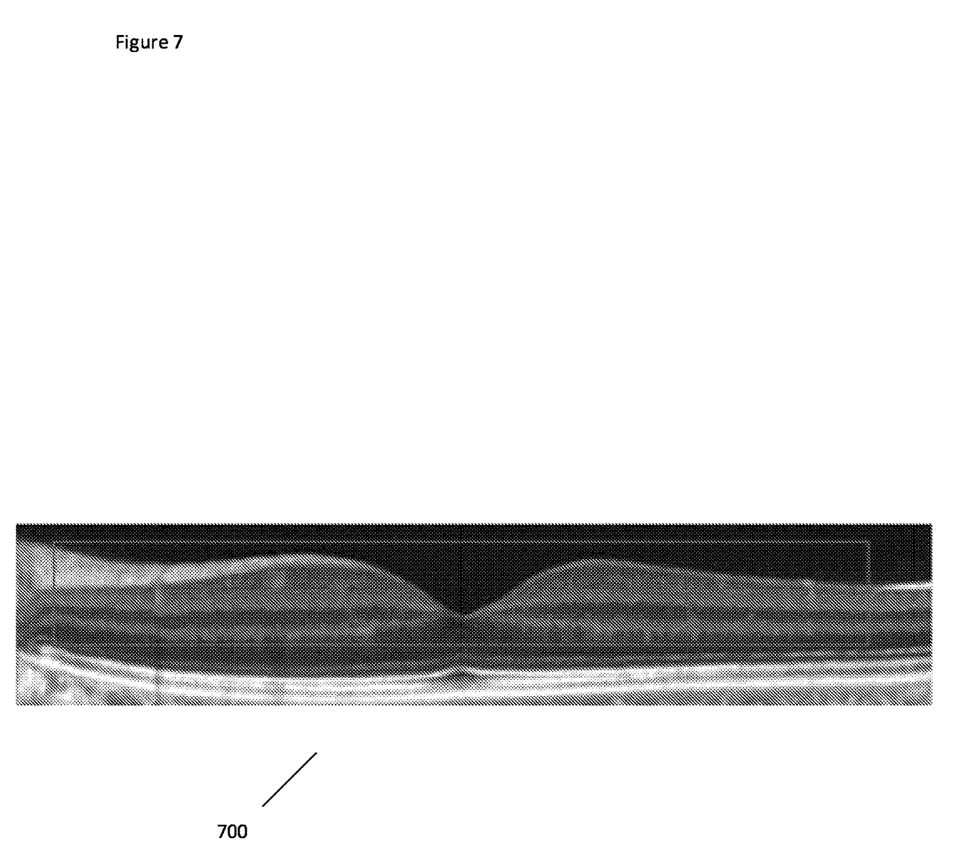
FIG. 7 shows an OCT section according to an embodiment of the invention.

Step 120 may comprise a sub-step 1210 of receiving structural data. The structural data may be indicative of a 3D structure of a neural retina of an eye. In some embodiments, the structural data may be derived from at least one optical coherence tomography (OCT) image. The OCT images may optionally be obtained as part of step 120 and stored in a memory accessible by control unit 210. In this case, the OCT images will be indicative of the structure of the neural retina of the particular eye of the subject for which the back-scattering spectrum is being determined in the method 100. Alternately, the OCT images may be obtained prior to method 100 and stored in a memory accessible by control unit 210. The OCT images may be indicative of structure of a different retina. An example slice 700 from an OCT scan of a retina is shown in FIG. 7. The structural data may, in some embodiments, be obtained from numerical modelling or other simulation of neural retinal structure.

Figure 8:
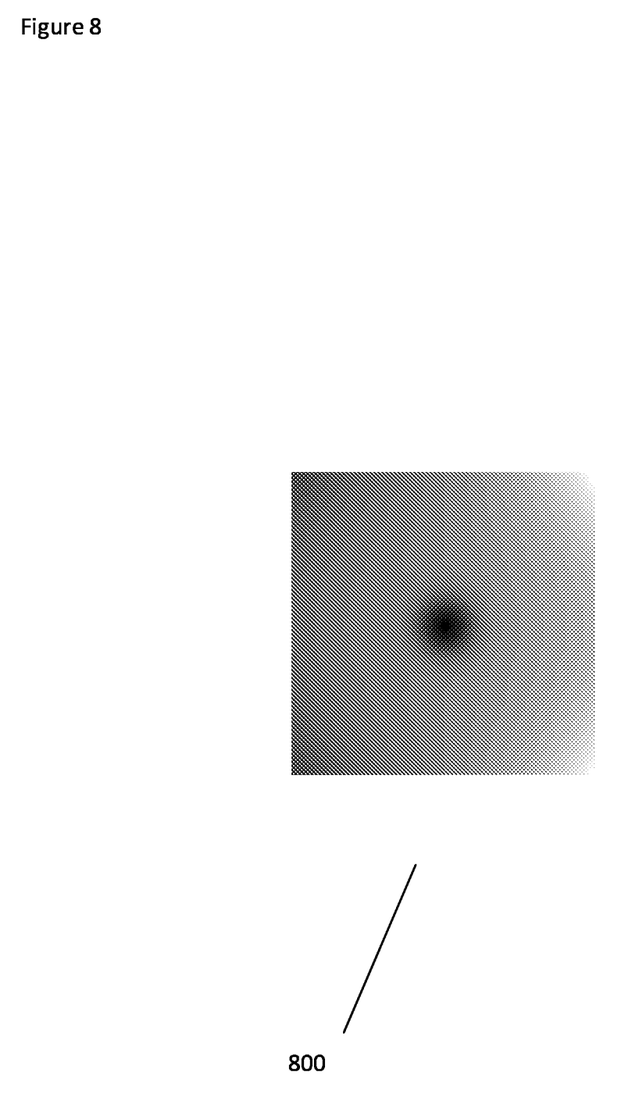
FIG. 8 shows a neural scatter template according to an embodiment of the invention.

Step 120 may comprise a sub-step 1220 of deriving a retinal map. The retinal map may be indicative of the reflectance characteristics of the neural retina. The retinal map may be derived from the structural data received in step 1210, for example the OCT images received in step 1210. The retinal map may be representable as an N×M pixel array wherein each pixel or cell of the pixel array is indicative of at least one reflectance property of the neural retina at that point or location of the neural retina for a given wavelength. For example, reflectance properties may include one or more of the thickness and the pigmentation of the neural retina. An example retinal map 800 is illustrated in FIG. 8. Dark pixels are indicative of a lower reflectance. Optionally, sub-step 1220 may comprise deriving a different retinal map for a plurality of wavelengths.

Step 120 may comprise a sub-step 1230 of scaling the retinal map. Sub-step 1230 may comprise receiving densitometer measurements of visual pigments in the retina. Sub-step 1230 may comprise fitting the densitometer measurements to known spectra of visual pigments, using the retinal map derived in step 1220 as a free parameter. Given that the back scatter from the neural retina is negligible at a fovea of the eye, a ratio of L to M cone cells can be quantified independently for the densitometer measurements. This allows the densitometer measurements to be compared to the known visual pigment spectra. Using the retinal map as a free parameter, an amplitude of correction may be derived in order to match the densitometer measurements to the known spectra. Sub-step 1230 may then comprise scaling the retinal map by the amplitude of correction.

Step 120 may comprise a sub-step 1240 of determining the second back-scattering spectrum. The second back-scattering spectrum may be determined in dependence on the scaled retinal map derived in sub-step 1230. The second back-scattering spectrum may comprise a plurality of back-scattering spectra, each corresponding to a spatial location on the neural retina. For example, each pixel of the retinal map may yield a back-scattering spectrum.

Sub-step 1240 may optionally comprise extrapolating the second back-scattering spectrum to other wavelengths. For example, sub-step 1240 may comprise extrapolating the second back-scattering spectrum to other wavelengths by using a Mie scattering model, analogously to sub-step 1130.

The method 100 comprises a step 130 of combining the spectra obtained in steps 110 and 120 to produce a back-scattering spectrum of an eye. The first back-scattering spectrum and the second back-scattering spectrum may be combined linearly, for example:

$$R_{scat}(\lambda) = RM_{scat}(\lambda) RN_{scat}(\lambda)$$

Where $RM_{scat}(\lambda)$ is the first back-scattering spectrum, $RN_{scat}(\lambda)$ is the second back-scattering spectrum and $R_{scat}(\lambda)$ is the combined back-scattering spectrum of the eye. However, other methods of combination, for example weighted combination, may be envisaged.

The resultant scattering spectrum $R_{scat}(\lambda)$ may be advantageously used to improve the determination of the optical density of visual pigments.

The optical density (OD) of visual pigments may be calculated using the reflectance difference between a dark adapted and a light bleached retina, due to the colour change in the visual pigments.

The OD may be calculated as $$OD_{visualpigment}(\lambda) = 0.5 \log 10 \left( \frac{R_{bleached}(\lambda)}{R_{darkadapted}(\lambda)} \right)$$

where $OD(\lambda)$ is the optical density as a function of wavelength, $R_{bleached}(\lambda)$ is the reflectance spectrum from a bleached eye as a function of wavelength, and $R_{darkadapted}(\lambda)$ is the reflectance spectrum from a dark-adapted eye as a function of wavelength. However, the effect of light scattering from optical media and the neural retina is not corrected for, and thus the reflectance spectra from the bleached and dark-adapted eyes will be contaminated with the scattering effect which will shift the resultant optical density spectra and cause inaccuracy.

Correcting for the scattering effect using the resultant scattering spectrum $R_{scat}(k)$ of method 100, the optical density may instead be calculated as:

$$OD_{visualpigment}(\lambda) = 0.5 \log 10 \left( \frac{R_{bleached}(\lambda) - R_{scat}(\lambda)}{R_{darkadapted}(\lambda) - R_{scat}(\lambda)} \right).$$

Figure 9:
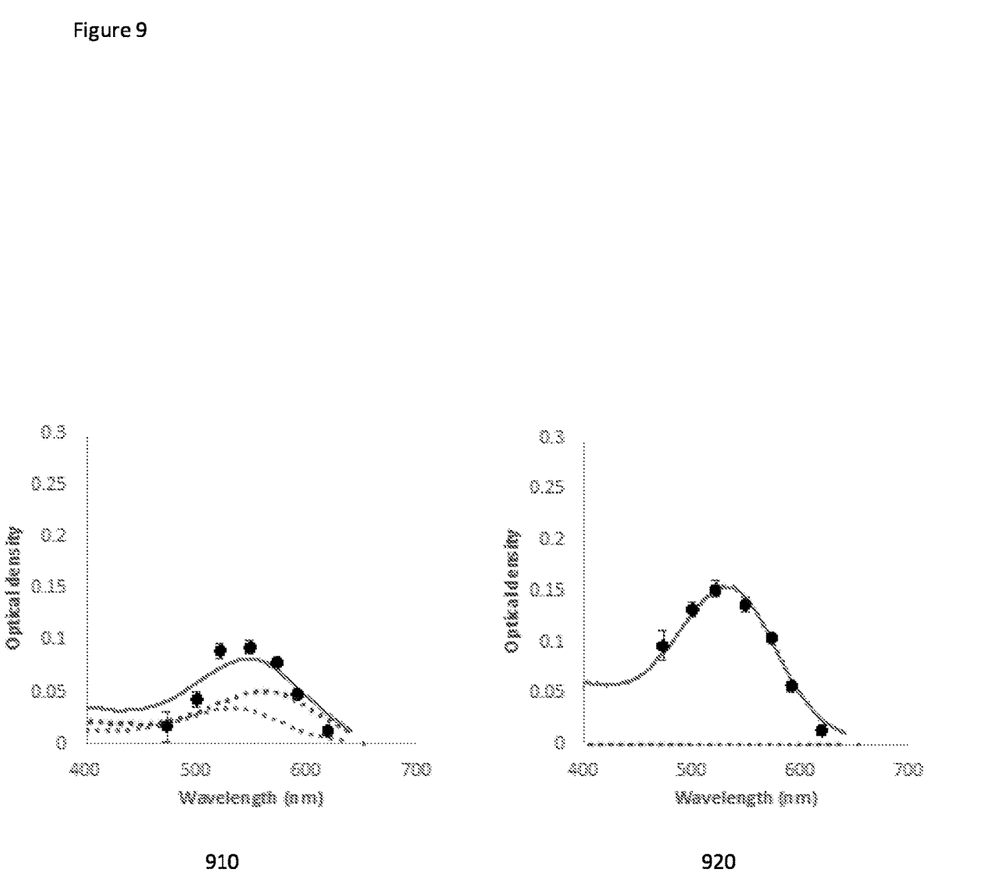
FIG. 9 shows contrasting visual pigment spectra with and without the implementation of an embodiment of the invention.

The contrasting optical density results with and without implementing the scatter correction of the present application are outlined in FIG. 9. FIG. 9 illustrates two optical density (OD) data sets 910 and 920 at a retinal location, without and with the implementation of scatter correction respectively. The data points illustrate the calculated optical densities at each wavelength. The dotted curves indicate the recovered 'm-cone' and 'l-cone' spectra.

In this case, the participant has protanopia, and only has 'm-cones' at the retinal location measured. The shift in measured optical density caused by the lack of scatter correction in data set 910 therefore causes the recovered spectra to erroneously suggest the person has both 'm-cone' and 'l-cone' pigments.

The scatter correction of method 100 causes the data 920 to be shifted to shorter wavelengths and increased in amplitude. The data now align perfectly with the known absorption characteristics of the 'm-cone' pigment and thus the optical density measurements have significantly increased in accuracy.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A computer-implemented method of determining a scattering spectrum of an eye, comprising:
   receiving data from a detector indicative of a reflected wave of radiation reflected from the retina, wherein the reflected wave of radiation is formed by an incident wave of masked radiation directed towards a retina of the eye, such that at least one region masked from the incident wave is present on the retina;
   determining a first back scattering spectrum indicative of light scattered from an optical media of the eye in dependence on a portion of the reflected wave of radiation corresponding to the at least one masked region;
   determining a second back scattering spectrum indicative of light scattered from a neural retina of the eye in dependence on retinal structure information representative of neural retinal structure; and determining the scattering spectrum of the eye in dependence on the first back scattering spectrum and the second back scattering spectrum
wherein the step of determining the second back scattering spectrum comprises:
receiving structural data indicative of a 3D structure of a neural retina;
deriving, from the structural data, a map of the neural retina; and
determining the second back scattering spectrum in dependence thereon.

2. The method of claim 1, wherein the first back scattering spectrum is indicative of light scattered from a lens of the eye.

3. The method of claim 1, wherein the at least one masked region extends linearly across the eye, or wherein the at least one masked region is arranged such that a plurality of masked regions alternate spatially with unmasked regions.

4. The method of claim 1, further comprising the steps of:
calculating, from the reflected wave of radiation, a reflectance corresponding to at least one of the masked regions; and
determining the first back scattering spectrum in dependence thereon.

5. The method of claim 1, wherein the radiation is EM radiation at least partially within the visible spectrum.

6. The method of claim 1, wherein the structural data is derived from optical coherence tomography (OCT) images.

7. Computer software which, when executed by a computer, is arranged to perform a method according to claim 1, wherein the step of determining the second back scattering spectrum comprises:
receiving structural data indicative of a 3D structure of a neural retina;
deriving, from the structural data, a map of the neural retina; and
determining the second back scattering spectrum in dependence thereon;
and the computer software is stored on a non-transitory computer readable medium.

8. Computer software which, when executed by a computer, is arranged to perform a method according to claim 1 and said method further comprising the step of extrapolating at least one of the first back scattering spectrum and the second back scattering spectrum to different wavelengths of incident radiation using a scattering model; and the computer software is stored on a non-transitory computer readable medium.

9. A computer-implemented method of determining a scattering spectrum of an eye, comprising:
receiving data from a detector indicative of a reflected wave of radiation reflected from the retina, wherein the reflected wave of radiation is formed by an incident wave of masked radiation directed towards a retina of the eye, such that at least one region masked from the incident wave is present on the retina;
determining a first back scattering spectrum indicative of light scattered from an optical media of the eye in dependence on a portion of the reflected wave of radiation corresponding to the at least one masked region;
determining a second back scattering spectrum indicative of light scattered from a neural retina of the eye in dependence on retinal structure information representative of neural retinal structure;
determining the scattering spectrum of the eye in dependence on the first back scattering spectrum and the second back scattering spectrum; and
extrapolating at least one of the first back scattering spectrum and the second back scattering spectrum to different wavelengths of incident radiation using a scattering model.

10. The method of claim 9, wherein the scattering model is a Mie scattering model.

11. A computer-implemented method for computing an optical density of visual pigments, comprising:
receiving a reflectance spectrum indicative of light reflected from a retina of a dark-adapted eye;
receiving a reflectance spectrum indicative of light reflected from a retina of a light-bleached eye;
determining a scattering spectrum; and
computing the optical density of visual pigments in dependence thereon,
wherein determining the scattering spectrum comprises:
receiving data from a detector indicative of a reflected wave of radiation reflected from the retina, wherein the reflected wave of radiation is formed by an incident wave of masked radiation directed towards a retina of the eye, such that at least one region masked from the incident wave is present on the retina;
determining a first back scattering spectrum indicative of light scattered from an optical media of the eye in dependence on a portion of the reflected wave of radiation corresponding to the at least one masked region;
determining a second back scattering spectrum indicative of light scattered from a neural retina of the eye in dependence on retinal structure information representative of neural retinal structure; and
determining the scattering spectrum of the eye in dependence on the first back scattering spectrum and the second back scattering spectrum.

12. The method of claim 11, wherein the step of computing the optical density is calculated as:

$$OD_{visualpigment}(\lambda) = 0.5 \log 10 \left( \frac{R_{bleached}(\lambda) - R_{scat}(\lambda)}{R_{darkadapted}(\lambda) - R_{scat}(\lambda)} \right)$$

where $OD(\lambda)$ is the optical density as a function of wavelength, $R_{bleached}(\lambda)$ is the reflectance spectrum from a bleached eye as a function of wavelength, $R_{darkadapted}(\lambda)$ is the reflectance spectrum from a dark-adapted eye as a function of wavelength, and $R_{scat}(\lambda)$ is the scattering spectrum as a function of wavelength.

13. The method of claim 11, wherein the step of determining the second back scattering spectrum comprises:
receiving structural data indicative of a 3D structure of a neural retina;
deriving, from the structural data, a map of the neural retina; and
determining the second back scattering spectrum in dependence thereon.

14. The method of claim 11, further comprising the step of extrapolating at least one of the first back scattering spectrum and the second back scattering spectrum to different wavelengths of incident radiation using a scattering model.

15. A device for determining a scattering spectrum of an eye, comprising:
- a radiation source for directing an incident wave of radiation towards a retina;
- a configurable mask for masking at least one area of the retina from the incident wave;
- a detector for detecting a reflected wave of radiation from the retina and outputting information indicative thereof;
- a processor configured to access the information indicative of the reflected wave and retinal structure information representative of neural retinal structure and to:
  - determine a first back scattering spectrum indicative of light scattered from an optical media of the eye in dependence on a portion of the reflected wave of radiation corresponding to the at least one masked region of the retina;
  - determine a second back scattering spectrum indicative of light scattered from a neural retina of the eye in dependence on the retinal structure information by receiving structural data indicative of a 3D structure of a neural retina, deriving, from the structural data, a map of the neural retina, and determining the second back scattering spectrum in dependence thereon; and
  - determine the scattering spectrum of the eye in dependence on the first back scattering spectrum and the second back scattering spectrum.

16. The device of claim 15, wherein the configurable mask is configured in use such that the at least one masked region extends linearly across the eye.

17. The device of claim 15, wherein the configurable mask is configured in use such that the at least one masked region comprises a plurality of masked regions.

18. The device of claim 17, wherein the plurality of masked regions of the eye alternate spatially with unmasked regions of the eye.

19. A device for determining a scattering spectrum of an eye, comprising:
- a radiation source for directing an incident wave of radiation towards a retina;
- a configurable mask for masking at least one area of the retina from the incident wave;
- a detector for detecting a reflected wave of radiation from the retina and outputting information indicative thereof;
- a processor configured to access the information indicative of the reflected wave and retinal structure information representative of neural retinal structure and to:
  - determine a first back scattering spectrum indicative of light scattered from an optical media of the eye in dependence on a portion of the reflected wave of radiation corresponding to the at least one masked region of the retina;
  - determine a second back scattering spectrum indicative of light scattered from a neural retina of the eye in dependence on the retinal structure information;
  - determine the scattering spectrum of the eye in dependence on the first back scattering spectrum and the second back scattering spectrum; and
  - extrapolate at least one of the first back scattering spectrum and the second back scattering spectrum to different wavelengths of incident radiation using a scattering model.

20. The device of claim 19, wherein the configurable mask is configured in use such that the at least one masked region extends linearly across the eye.

21. The device of claim 19, wherein the configurable mask is configured in use such that the at least one masked region comprises a plurality of masked regions.

22. The device of claim 21, wherein the plurality of masked regions of the eye alternate spatially with unmasked regions of the eye.

* * * * *